United States Patent [19]

Higa

[11] Patent Number: 5,591,634
[45] Date of Patent: Jan. 7, 1997

[54] MICROBIOLOGICAL METHOD FOR DISPOSING OF ORGANIC WASTE MATERIALS

[76] Inventor: Teruo Higa, 509, Aza Shimashi, Ginowan-shi, Okinawa-ken, Japan

[21] Appl. No.: 531,124

[22] Filed: Sep. 20, 1995

Related U.S. Application Data

[63] Continuation of Ser. No. 82,094, Jun. 24, 1993, abandoned.

[51] Int. Cl.$^6$ .................... C05F 9/00; C12S 13/00
[52] U.S. Cl. ................................ 435/262; 435/267
[58] Field of Search ......................... 426/262, 267

[56] References Cited

U.S. PATENT DOCUMENTS

| | | | |
|---|---|---|---|
| 4,582,514 | 4/1986 | Kneer | 55/71 |
| 4,985,060 | 1/1991 | Higa | 71/6 |

FOREIGN PATENT DOCUMENTS

| | | |
|---|---|---|
| 9104361 | 2/1993 | Brazil . |
| 9103618 | 3/1993 | Brazil . |

OTHER PUBLICATIONS

Kobayashi et al. CA 111(14):120306m 1988.
Kobayashi et al. CA(102)(16):137267m 1984.
Higa, T. CA 119(17):179373z 1993.
Higa, T CA 119(16):167119h 1993.
Higa, T. CA 119(16):167118g 1993.

*Primary Examiner*—Carolyn Paden
*Attorney, Agent, or Firm*—Ladas & Parry

[57] ABSTRACT

Disclosed herein are a method for disposing of organic waste materials using microorganisms; methods for accelerating the growth of plants, for destroying or repelling insect pests, for improving the soil, of deodorization and for improving water quality, using the waste materials processed by the disposal method; and compositions for use in these methods. The microbiological method for disposing of an organic waste material comprises the step of bringing (i) an organic waste material into contact with (ii) at least 5 species of microorganisms, each being selected from each of 5 groups consisting of actinomycetes, phototrophic bacteria, lactic acid bacteria, mold fungi and yeast, the microorganisms (a) being acid-fast, (b) capable of producing lactic acid, (c) producing no butyric acid, (d) being non-pathogenic and (e) having an antagonistic value of 50 or more.

3 Claims, No Drawings

MICROBIOLOGICAL METHOD FOR DISPOSING OF ORGANIC WASTE MATERIALS

This is a continuation of application Ser. No. 08/082,094 filed on Jun. 24, 1993, now abandoned.

BACKGROUND OF THE INVENTION

1. Field of the Invention

The present invention relates to a method for disposing of organic waste materials using microorganisms, and a use of the waste materials processed by this disposal method. More specifically, the present invention relates to a method for disposing of organic waste materials; methods for accelerating the growth of plants, for destroying or repelling insect pests, for improving the soil, for deodorizing unpleasant odors and for improving water, using the waste materials processed by the disposal method; and compositions for use in these methods.

2. Related Art

One of the problems facing society is how to efficiently dispose of organic wastes and sometimes to effectively utilize these wastes once they have been disposed.

For instance, liquid waste discharged in a process of alcohol production has been utilized as livestock feed or an organic fertilizer put on fields. However, this liquid waste deteriorates quickly, so that its utilization is limited. In addition, when this liquid waste flows into rivers, the biochemical oxygen demand (BOD) increases drastically, threatening the ecosystem of the rivers with destruction. Furthermore, since the liquid waste has potent reducing power, there is a possibility that soil and underground water are polluted when the liquid waste permeates the soil. For these reasons, it is the present situation that the liquid waste is, in most cases, handled and disposed as industrial waste, not used efficiently.

An effective method for disposing of the above liquid waste has not been found so far. Because the liquid waste discharged in the process of alcohol production contains organic acids, it exhibits high acidity at the outset of discharge. The liquid waste is however alkalized swiftly as the oxidization thereof proceeds. This alkalization brings about a rapid increase of anaerobic putrefying bacteria such as butyric acid bacteria. As a result, the liquid waste produces extremely strong unpleasant odors. Furthermore, since the protein and the amino acid contents of this liquid waste are extremely high, large quantities of hydrogen sulfide, ammonia, mercaptan and the like are produced in the degenerating process of the liquid waste. It has been said that an unpleasant odor released from a mixture of the above compounds produced and acetic acid has a nature of the worst kind.

In general, the liquid waste discharged in the process of alcohol production is alkalized, specifically to a pH of 8 or more. Under such conditions, ordinary microorganisms cannot be active. For this reason, it cannot be expected that the liquid waste is degraded by spontaneous microorganisms. The liquid waste thus produces unpleasant odors over a long period of time.

In addition to a method for disposing of the liquid waste discharged in the process of alcohol production, it is also desired to devise a method for disposing of organic waste materials such as raw garbage produced by households or eating establishments, wastes produced in the processing of agricultural or marine products, excrements of domestic animals and sewage.

Since the above organic waste materials contain a large amount of water, it is necessary to feed a large quantity of air into them or to agitate them frequently in order to decompose them aerobically. When the wastes are not decomposed aerobically, harmful fermentation proceeds and produces unpleasant odors. However, the above operation for causing the aerobic decomposition requires an installation for the treatment and also increases the running cost.

SUMMARY OF THE INVENTION

An object of the present invention is to provide a method for disposing of organic waste materials.

Another object of the present invention is to provide a method for disposing of organic waste materials, the waste materials processed by the disposal method being effectively reusable.

We have now found that the above objects of the present invention can be accomplished by a microbiological method of disposal, utilizing microorganisms having a specific nature.

According to the present invention, there provides a microbiological method for disposing of an organic waste material comprising the step of bringing (i) an organic waste material into contact with (ii) at least 5 species of microorganisms, each being selected from each of 5 groups consisting of actinomycetes, phototrophic bacteria, lactic acid bacteria, mold fungi and yeast, the microorganisms (a) being acid-fast, (b) capable of producing lactic acid, (c) producing no butyric acid, (d) being non-pathogenic and (e) having an antagonistic value of 50 or more, under the closed and airtight conditions at a pH of 3.0 to 5.0.

We have also unexpectedly found that the waste materials processed by the above disposal method can be utilized for improving the soil, destroying or repelling insect pests, deodorizing an unpleasant odor and improving water quality.

Therefore, a further object of the present invention is to provide methods for accelerating the growth of plants, for improving the soil, for destroying or repelling insect pests, of deodorizing an unpleasant odor and for improving water, and compositions for use in these methods.

DETAILED DESCRIPTION OF THE INVENTION

Organic Waste Materials

The disposal method of the present invention can be applied to, for example, liquid waste discharged in the process of alcohol production (for instance, liquid waste discharged in the manufacturing process of distilled liquor, beer, Japanese sake or the like), raw garbage produced by households or eating establishments, wastes produced in the processing of agricultural or marine products (for instance, fish bones and fish bodies discarded by fish processing factories), excrements of domestic animals and city sewage.

In particular, processed waste obtained by applying the method of the present invention to liquid waste discharged in the process of alcohol production can be favorably utilized for improving the soil, for accelerating the growth of plants, for destroying or repelling insect pests (specifically, protection of plants or animals by destroying or repelling insect pests, and control of ants such as leaf-cutting ants and termites), for deodorizing unpleasant odors and for improving water quality.

Processed waste obtained by applying the method of the present invention to garbage, wastes produced in the processing of agricultural or marine products, or excrements of domestic animals can be favorably used for accelerating the growth of plants, i.e., as fertilizer.

The method according to the present invention can be applied to the above-mentioned organic waste materials without treating them in advance. However, when the organic waste materials are garbage, wastes produced in the processing of agricultural or marine products, or excrements of domestic animals, it is preferable to apply the method of the present invention after adjusting the pH of the waste materials to 3.0 to 5.0, more preferably 3.0 to 4.5 with an organic acid. An example of a suitable organic acid is a straight or branched chain, saturated or unsaturated carboxylic acid having 2 to 6 carbon atoms. Specific examples of such an acid include acetic acid, lactic acid, citric acid, malic acid, ascorbic acid and gluconic acid. Lactic acid is most preferred from the viewpoints of its ability to prevent the activity of putrefying bacteria, and its ability to prevent sudden changes in pH level as compared to other organic acids.

Microorganisms

In the method of the present invention, at least 5 species of microorganisms, each being selected from each of 5 groups consisting of actinomycetes, phototrophic bacteria, lactic acid bacteria, mold fungi and yeast, are employed. It is necessary that all of the microorganisms belonging to each group have the properties of (a) being acid-fast, (b) producing lactic acid, (c) producing no butyric acid, (d) being non-pathogenic and (e) having an antagonistic value of 50 or more. To have an antagonistic value of 50 or more is herein intended to mean that microorganisms have antibacterial power of suppressing the growth of 50% or more hyphae of Fusarium cultured in agar media under the conditions of 24 hours of cultivation.

In the method according to the present invention, at least one specie of microorganism is selected from each of the above five groups. Without intending to be bound by theory, it is believed that the microorganisms having the above-mentioned properties, at least one species of microorganism being selected from each of the above five groups, optionally together with those microorganisms contained in an organic waste material, cause continuous and efficient degradation of the organic waste. For instance, phototrophic bacteria digest various components such as ammonia, hydrogen sulfide and mercaptan, and decompose the sources of unpleasant odors and, at the same time, promote the formation of a variety of useful amino acids such as proline and methionine. Lactic acid bacteria prevent an unfavorable decomposing process. Furthermore, it is considered that actinomycetes and yeast suppress the activity of harmful microorganisms unfavorably existing in the processed wastes, thereby contributing to the formation of a colony of Gram-positive bacteria.

According to the preferred embodiment of the present invention, it is preferable to employ microorganisms, two or more species of microorganisms selected from each of the above five groups. It can be expected that organic wastes are degraded more efficiently by various enzymes derived from these microorganisms.

Any microorganism can be used as long as it has the above-mentioned mycological properties. Preferable specific examples of such microorganisms are as follows:

Actinomycetes include for example microorganisms belonging to Streptomyces, Streptoverticillium, Nocardia, Micromonospora and Rhodococcus. Specific examples of actinomycetes include *Streptomyces albus* (e.g. ATCC 3004), *Streptoverticillium baldaccii* (e.g. ATCC 23654), *Nocardia asteroides* (e.g. ATCC 19247), *Micromonospora chalcea* (e.g. ATCC 12452) and *Rhodococcus rhodochrous* (e.g. ATCC 13803).

Phototrophic bacteria include for example microorganisms belonging to Rhodopseudomonas, Rhodospirillum, Chromatium, and Chlorobium. Specific examples of phototrophic bacteria include *Rhodopseudomonas sphaeroides* (e.g. IFO 12203), *Rhodospirillum rubrum* (e.g. IFO 3986), *Chromatium okenii* and *Chlorobium limicola*.

Lactic acid bacteria include for example microorganisms belonging to Lactobacillus, Propionibacterium, Pediococcus and Streptococcus. Specific examples of lactic acid bacteria include *Lactobacillus bulgaricus* (e.g. ATCC 11842), *Propionibacterium freudenreichii* (e.g. IFO 12391), *Pediococcus halophilus* (e.g. IFO 12172), *Streptococcus lactis* (e.g. IFO 12007) and *Streptococcus faecalis* (e.g. IFO 3971).

Mold fungi include for example microorganisms belonging to Aspergillus and Mucor. Specific examples of these mold fungi include *Aspergillus japonicus* (e.g. IFO 4060), *Aspergillus oryzae* (e.g. IFO 4075) and *Mucor hiemalis* (e.g. IFO 5303).

Yeast include for example microorganisms belonging to Saccharomyces and Candida. Specific examples of these yeast include *Saccharomyces cerevisiae* (e.g. IFO 0304), *Saccharomyces lactis* (e.g. IFO 0433) and *Candida utilis* (e.g. IFO 0396).

While these microorganisms can be used as they are, it is preferable to use those microorganisms which are pre-cultured in a proper culture medium. The pre-culture is preferably conducted in a proper culture medium with a pH of 3.0 to 5.0 at a temperature in the range of approximately 25° to 45° C. No particular limitation is imposed on the culture medium which is used for this pre-culture.

Degradation of Organic Waste Materials

In the present invention, an organic waste material is microbiologically degraded when it is brought into contact with the above microorganisms under closed and airtight conditions, i.e., anaerobic condition, at a pH from 3.0 to 5.0.

There is no particular limitation on the manner how to bring the microorganisms into contact with the organic waste material. It is however general to add the microorganisms as they are or the above pre-culture solution to the organic waste material. It is also possible to place the microorganisms which are supported on a specific carrier in the organic waste material.

The treatment temperature is preferably in the range of approximately 25° to 45° C. In the case where the temperature is lower than 25° C., many hours are required for the treatment. On the other hand, when the temperature is higher than 45° C., a side reaction tends to occur. In general, the treatment conducted under the above conditions is completed after about 72 to 96 hours.

Use of Processed Wastes

The waste materials processed by the disposal method of the present invention never pollute the environment even when they are discharged into the environment as they are. It is therefore possible to discard the processed wastes in the natural environment as they are.

However, it is surprising that the waste materials processed by the disposal method of the present invention have various activities, so that they can be utilized effectively.

According to the preferred embodiment of the present invention, the processed wastes can be used for the purposes of improving the soil, accelerating the growth of plants, destroying or repelling insect pests (specifically, protection of plants or animals by destroying or repelling insect pests, and control of ants such as leaf-cutting ants and termites), deodorizing an unpleasant odor and improving water quality.

While the processed wastes per se are used for the above uses, it is preferable to use the processed wastes by diluting them with a proper vehicle such as water.

How to use the processed waste and the amount thereof can be properly selected depending on the species of an organic waste material used, the concentration of the organic waste, and a use of the processed waste. For example, in order to use the processed waste as fertilizer (i.e., a plant growth accelerating agent), about 500 to 5,000 g/m$^2$, preferably about 1,000 to 2,000 g/m$^2$ of the processed waste diluted preferably with water to approximately 1/100 to 1/200 is spread over the soil.

In order to improve the soil, about 3,000 to 10,000 g/m$^2$, preferably about 4,000 to 5,000 g/m$^2$ of the processed waste diluted preferably with water to approximately 1/1,000 to 1/10,000 is spread over the soil.

In order to destroy or repel insect pests, about 50 to 500 g/m$^2$, preferably about 100 to 200 g/m$^2$ of the processed waste diluted preferably with water to approximately 1/50 to 1/500 is spread over the soil, or directly applied to plant or animal bodies. Moreover, the processed waste of the present invention can also be applied directly to insect pests to be destroyed or repelled, or to their nests.

For the purpose of deodorizing an unpleasant odor, about 300 to 1,000 g/m$^2$, preferably about 400 to 500 g/m$^2$ of the processed waste diluted preferably with water to approximately 1/200 to 1/300 is applied to the source of the unpleasant odor.

In order to improve water quality, about 300 to 1,000 g/m$^3$, preferably about 400 to 500 g/m$^3$ of the processed waste diluted preferably with water to approximately 1/3 to 1/5 is put in sewage.

The present invention will now be explained more specifically by referring to the following examples, which should not be construed as limiting the present invention.

EXAMPLE 1

Disposal of Liquid Waste Discharged in the Process of Alcohol Production, Using Microorganisms The following microorganisms were employed:

*Streptomyces albus* (ATCC 3004), *Streptoverticillium baldaccii* (ATCC 23654), *Nocardia asteroides* (ATCC 19247) and *Micromonospora chalcea* (ATCC 12452) as microorganisms belonging to actinomycetes;

*Rhodopseudomonas sphaeroides* (IFO 12203), *Rhodospirillum rubrum* (IFO 3986) and *Chromatium okenii* as microorganisms belonging to phototrophic bacteria;

*Lactobacillus bulgaricus* (e.g. ATCC 11842), *Propionibacterium freudenreichii* (e.g. IFO 12391), *Pediococcus halophilus* (e.g. IFO 12172), *Streptococcus lactis* (e.g. IFO 12007) and *Streptococcus faecalis* (e.g. IFO 3971) as microorganisms belonging to lactic acid bacteria;

*Aspergillus japonicus* (IFO 4060), *Aspergillus oryzae* (IFO 4075) and *Mucor hiemalis* (IFO 0433) as microorganisms belonging to mold fungi; and

*Saccharomyces cerevisiae* (IFO 0304), *Saccharomyces lactis* (IFO 0433) and *Candida utilis* (IFO 0396) as microorganisms belonging to yeast.

These microorganisms were added to 10 liters of liquid waste discharged in the process of alcohol production (liquid waste discharged in the manufacturing process of distilled spirits utilizing theriac) while the liquid waste had a pH of 3.0 to 5.0. Cultivation of the microorganisms was conducted at a temperature of 25° to 35° C. under the closed and airtight conditions, and carried on until the generation of gas was completed and the culture solution steadily showed a pH of 3.0 to 4.0. The culture solution thus obtained was preserved in an airtight container.

EXAMPLE 2

Soil Improvement and Plant-Growth Acceleration

The culture solution obtained in Example 1 was diluted with water to 1/1000. The resulting solution was spread over a field twice.

The soil was analyzed in terms of elements contained therein. Furthermore, peanut was planted in the field. The yield of this was compared with nontreated field. The results are as shown in Table 1.

TABLE 1

|  | Total Nitrogen (mg %) | Available Phosphorous (ppm) | K (mg %) | Ca (mg %) | Mg (mg %) |
| --- | --- | --- | --- | --- | --- |
| Treated | 145 | 21 | 10 | 504 | 23 |
| Non-treated | 128 | 9 | 10 | 417 | 19 |

|  | Total organic substance (%) | pH | Yield (Kg/20 m$^2$) | Gas phase rate in the soil (%, at 25 cm) |
| --- | --- | --- | --- | --- |
| Treated | 1.5 | 6.6 | 33.1 | 43 |
| Untreated | 0.7 | 6.2 | 20.6 | 20 |

EXAMPLE 3

Control of Disease and Insect Pests (Protection of Plants)

The culture solution obtained in Example 1 was diluted with water to 1/500. The resulting solution was sprayed three times upon the leaves of cabbages cultivated by a general manner.

The rate of incidence of disease and that of generation of insect pests in the cabbages were compared with those in untreated cabbages. The results are as shown in Table 2.

TABLE 2

|  | *Plutella maculipennis* (%) | Aphids (%) | *Agrotis fuscosa* (%) | Mould disease (%) | Commercialized rate (%) |
| --- | --- | --- | --- | --- | --- |
| Treated | 5 | 0 | 5 | 10 | 98 |
| Non-treated | 100 | 100 | 20 | 100 | 10 |

EXAMPLE 4

Deodorization

The culture solution obtained in Example 1 was diluted with water to 1/500. A pigsty was entirely sprinkled with the solution every 5 days, 3 times in total. An analysis was conducted in terms of the compounds which are the sources of unpleasant odors before and after the sprinkling. The results are as shown in Table 3.

TABLE 3

| Compounds | Before treatment | After treatment |
| --- | --- | --- |
| Ammonia | 3.3 ppm | 0.06 ppm |
| Hydrogen sulfide | 0.139 ppm | ND |
| Methyl mercaptan | 0.036 ppm | ND |
| Methyl sulfide | ND | ND |
| Trimethylamine | 0.024 ppm | ND |

*ND: not detected

EXAMPLE 5

Water Quality Improvement

The culture solution obtained in Example 1 was placed in a tank of a purifier capable of purifying sewage from 300 persons per day in average, in an amount of 1/1000 of the capacity of the tank. The water quality was examined and the amount of sludge accumulated was measured. The results are as shown in Table 4.

TABLE 4

| | Before Treatment | After Treatment (days) | | | | |
| --- | --- | --- | --- | --- | --- | --- |
| | ment | 30 | 60 | 120 | 240 | 360 |
| BOD (ppm) | 290 | 30 | 20 | 15 | 5 | 3 |
| SS (ppm) | 500 | 50 | 30 | 20 | 3 | 2 |
| Sludge in a month | 2 tons | 200 kg | 110 kg | 100 kg | 75 kg | 75 kg |
| E. coli | $5 \times 10^5$ | $3 \times 10^3$ | $1 \times 10^3$ | 0 | 0 | 0 |

BOD is biochemical oxygen demand and SS is suspended solids.

EXAMPLE 6

Control of Insect Pests (Protection of Animals)

The culture solution obtained in Example 1 was diluted with water to 1/100. The resulting solution was applied to the entire body of a pig. The numbers of ticks and botflies on the surface of the pig's body were respectively counted. The results are as shown in Table 5.

TABLE 5

| | | Treatment Times | | |
| --- | --- | --- | --- | --- |
| | Untreatment | 1 | 2 | 3 |
| Tick (/30 cm$^2$) | 62 | 2 | 0 | 0 |
| Botfly (/30 cm$^2$) | 40 | 6 | 2 | 0 |

EXAMPLE 7

Control of Leaf-cutting Ants

The culture solution obtained in Example 1 was diluted with water to 1/100. The resulting solution was injected into a nest of leaf-cutting ants. Change in the activity of the ants before and after the injection was observed. The results are as shown in Table 6.

TABLE 6

| Number of | Ant's activity after treatment | | |
| --- | --- | --- | --- |
| nest treated | 15 days | 30 days | 60 days |
| 5 | Partly active | No activity | No activity |

EXAMPLE 8

Control of Termites

The culture solution obtained in Example 1 was diluted with water to 1/500. The resulting solution was injected into a nest of termites to thoroughly infiltrate the entire nest with the solution. The surface of the nest became soft every time it rained. The nest was then finally decayed. The state of the decay was as shown in Table 7. As is clear from the table, the nest was completely decayed 120 days after the treatment.

TABLE 7

| Number of | Stage of decay of nests after treatment | | |
| --- | --- | --- | --- |
| nest treated | 30 days | 60 days | 120 days |
| 5 | 0% | 20% | 100% |

EXAMPLE 9

Barnyard Manure as Fertilizer

After barnyard manure from a pigsty which had been treated in Example 4 was applied to a field, spinach was cultivated in the field. The spinach thus produced was compared with spinach produced from untreated field. The results are as shown in Table 8.

TABLE 8

| | Treated plot | Untreated plot |
| --- | --- | --- |
| Weight (g) (average of 10 plants) | 335 | 145 |
| Maximum height (cm) | 20.2 | 15.8 |
| Number of leaves per plant (5 cm or more in size) | 7.8 | 5.2 |

EXAMPLE 10

Control of Nematodes

The culture solution obtained in Example 1 was diluted with water to 1/1000. the resulting solution was spread over a field four times in total, one time one week before dissemination of carrot seeds, and three times every two weeks after germination thereof. The nematode-damaged rate in the carrots thus produced was compared with that in carrots produced from an untreated field. The results are as shown in Table 9.

TABLE 9

|  | Untreated plot | Treated plot |
|---|---|---|
| Trial No. 1 | 80% | 5% |
| Trial No. 2 | 87% | 0% |

EXAMPLE 11

Production of Manure from Garbage

Microorganisms which were the same as those used in Example 1 were added to a mixture of 70 g of rice bran, 20 g of oil cake and 10 g of fish waste. To this mixture, water was added so that the resulting mixture would contain 50% (w/w) of water. Thereafter, the microorganisms were cultured at a temperature of 25° to 30° C. for 4 days. The mixture thus obtained was mixed with kitchen garbage (pH=4.0) at the rate of 50 g per 10 kg of the garbage. It is noted that the garbage had been moistened with a 0.2% aqueous solution of lactic acid in advance. The resulting mixture was placed in a plastic bag. The bag was sealed up, and stored at a temperature of 25° to 30° C. for 14 days.

After the garbage thus processed was spread over a field at the rate of 2 liters per square meter, dentata was cultivated in this field. The dentata thus produced and dentata produced from the control plot were compared. The results are as shown in Table 10.

In the control plot, 30 g of nitrogen, 30 g of phosphorus and 24 g of potassium were given per 1 $m^2$.

TABLE 10

|  | Height (cm) | Weight (g) | Yield (Kg/lm$^2$) |
|---|---|---|---|
| Treated plot | 35 | 53 | 5.3 |
| Control plot | 30 | 40 | 4 |

EXAMPLE 12

Disposition of Fish Waste and Excrement of Pig Waste

Microorganisms which were the same as those used in Example 1 were added to fish broth (pH=3.5), and cultivated at a temperature of 34° to 36° C. for 4 days. 100 ml of this culture solution was added to 80 liters of a mixture consisting of 50% by weight of fish waste and 50% by weight of excrement of pig, whose pH had been adjusted to 3.5 by lactic acid in advance. The resulting mixture was placed in an airtight container, and the container was preserved at a temperature of 35° C. After 48 hours, the supernatant liquid of the mixture was removed, and the pH of the remaining mixture was adjusted to 3.5 by lactic acid. The container was further preserved at a temperature of 35° C. for 48 hours. It was then sealed up, and allowed to stand at room temperature until the generation of gas was completed.

EXAMPLE 13

Fertilizer Obtained from Fish Waste and Excrement of Pig

The solution obtained in Example 12 was spread over a field at the rate of 2 liters per square meter. Tomato plants were planted in this field. The tomatoes thus produced and tomatoes produced from the control field were compared. The results are as shown in the following Table 11.

In the control field, 30 g of nitrogen, 30 g of phosphorus and 24 g of potassium were given per 1 $m^2$. Six tomato plants were planted in each plot.

TABLE 11

|  | Number of tomatoes per plant | Yield (kg/plant) | Average sugar content |
|---|---|---|---|
| Treated plot | 9 | 9.2 | 6.0 |
| Control plot | 7 | 5.6 | 6.0 |

EXAMPLE 14

Deodorizing Effect of Processed Waste Obtained from Fish Waste and Excrement of Pig The solution obtained in Example 12 was applied to the source of unpleasant odors. Change in the concentration of the compounds producing the unpleasant odor before and after the treatment was measured. The results are as shown in Table 12.

TABLE 12

| Compounds | Before treatment (ppm) | After treatment (ppm) |
|---|---|---|
| Ammonia | 19.2 | ND |
| Hydrogen sulfide | 0.58 | ND |
| Methyl mercaptan | 0.16 | ND |
| Methyl sulfide | 0.11 | ND |
| Trimethylamine | 0.14 | ND |

*ND: not detected

What is claimed is:

1. A microbiological method for microbiologically degrading an organic waste material comprising a. adjusting the pH of the waste material to 3.0 to 5.0 with an organic acid;

b. incubating the organic waste material with at least one member of actinomycetes, one member of phototropic bacteria, one member of lactic acid bacteria, one member of mold fungi and one member of yeast, the at least one member of actinomycetes selected from *Streptomyces albus*, *Streptoverticilliu baldaccii*, *Nocardia asteroides*, *Micromonospora chalcea* or *Rhodoccus rhodochrous*; the at least one member of phototrophic bacteria selected from *Rhodopseudomonas sphaeroides*, *Rhodospirillum rubrum*, *Chromatium okenii*, or *Chlorobium limicola*; the at least one member of lactic acid bacteria selected from the group *Lactobacillus bulgaricus*, *Propionibacterium freudenreichii*, *Pediococcus halophilus*, *Streptococcus lactis* or *Streptococcus faecalis*; and the at least one member of mold fungi selected from *Aspergillus japonicus*, *Aspergillus oryzae* or *Mucor hiemalis*; and the at least one member of yeast selected from the group *Saccharomyces cerevisiae*, *Saccharomyces lactis* or *Candia utili* and incubating said microorganisms with the organic waste material under airtight conditions at a temperature of 45° C. or less, and under conditions sufficient to degrade the organic waste material wherein the organic waste material is selected from the group consisting of liquid wastes discharged in the process of alcohol production, garbage produced by households or eating establishments, wastes produced in the processing of agricultural or marine products, excrements of domestic animals and sewage.

2. The method according to claim 1, wherein the incubation is carried out at a temperature from 25° C.–45° C.

3. The method according to claim 1, wherein the microorganisms are incubated with the organic waste material for about 72 to 96 hours.

* * * * *